US00PP13293P2

(12) United States Plant Patent
Olesen et al.

(10) Patent No.: US PP13,293 P2
(45) Date of Patent: Dec. 3, 2002

(54) HYBRID TEA ROSE PLANT NAMED 'POULSCOTS'

(76) Inventors: L. Pernille Olesen, Hillerødvejen 49, DK-3480, Fredensborg (DK); Mogens N. Olesen, Hillerødvejen 49, DK-3480, Fredensborg (DK)

( * ) Notice: Subject to any disclaimer, the term of this patent is extended or adjusted under 35 U.S.C. 154(b) by 0 days.

(21) Appl. No.: 09/774,821

(22) Filed: Jan. 30, 2001

(51) Int. Cl.[7] ..... A01H 5/00
(52) U.S. Cl. ..... Plt./130
(58) Field of Search ..... Plt./130

(56) References Cited

PUBLICATIONS

UPOV–ROM GTITM Computer Database, 2001/06, GTI Jouve Retrieval Software, citation for 'Poulscots'.*

* cited by examiner

*Primary Examiner*—Bruce R. Campell
*Assistant Examiner*—Susan B. McCormick

(57) ABSTRACT

A new Hybrid Tea garden rose plant which has abundant, lavender flowers and attractive foliage. This new and distinct variety has shown to be uniform and stable in the resulting generations from asexual propagation.

1 Drawing Sheet

CLASSIFICATION

Botanical: *Rosa hybrida* 'POULscots'.

Commercial: Shrub.

SUMMARY OF THE INVENTION

The present invention constitutes a new and distinct variety of garden rose plant which originated from a controlled crossing between 'POULari' described and illustrated in U.S. Plant Pat. No. 9,274 issued on Sep. 5, 1994 and 'Mainzer Fastnacht' (TANsi), an unpatented variety. The two parents were crossed during the spring of 1989 and the resulting seeds were planted in a controlled environment in Fredensborg, Denmark. The new variety is named 'POULscots'.

The new rose may be distinguished from its seed parent, 'POULari', by the following combination of characteristics:

1. 'POULscots' exhibits lavender blooms; whereas 'POULari' exhibits white blooms.

2. 'POULscots' has fewer petals than 'POULari'.

3. The blooms of 'POULscots' are borne singly, whereas 'POULari' exhibits multiple blooms per stem.

The new variety may be distinguished from its pollen parent, 'Mainzer Fastnacht' by the following combination of characteristics:

1. 'POULscots' exhibits lighter lavender blooms when compared to the pollen parent.

2. 'POULscots' has softer petals when compared to the pollen parent.

3. 'POULscots' has more glossy foliage than 'Mainzer Fastnacht'.

The objective of the hybridization of this rose variety was to create a new and distinct variety for garden use with unique qualities, such as:

1. Uniform and abundant flowers.

2. Vigorous, but compact growth when propagated both as a budded rose and on its own roots;

3. Disease resistance.

This combination of qualities is not present in previously available commercial cultivars of this type and distinguish 'POULscots' from all other varieties of which we are aware.

As part of their rose development program, L. Pernille Olesen and Mogens N. Olesen germinated the seeds from the aforementioned hybridization during winter 1990 and conducted evaluations on the resulting seedlings in a controlled environment in Fredensborg, Denmark.

'POULscots' was selected in the spring 1991 by the inventors as a single plant from the progeny of the aforementioned hybridization. Asexual reproduction of 'POULscots' by traditional budding and rooted cuttings was first done by L. Pernille and Mogens N. Olesen in their nursery in Fredensborg, Denmark in summer 1991. This initial and other subsequent asexual propagations conducted in controlled environments have demonstrated that the characteristics of 'POULscots' are true to type and are transmitted from one generation to the next.

BRIEF DESCRIPTION OF THE DRAWING

The accompanying color illustration shows as true as is reasonably possible to obtain in color photographs of this type the rose variety 'POULscots'. Specifically illustrated in SHEET 1 are 'POULscots' foliage, flower buds, partially opened buds, and an open bloom.

DETAILED DESCRIPTION OF THE VARIETY

The following is a description of 'POULscots', as observed in its growth during trials at the testing station Prüfstelle Rethmar under the testing authority Bundessortenamtin in Hannover, Germany and at the inventor's nursery in Fredensborg, Denmark. Color references are made using The Royal Horticultural Society (London, England) Colour Chart, 1995, except where color terms of color are used.

For a comparison, several physical characteristics of the rose variety 'POULari', a rose variety from the same inventors described and illustrated in U.S. Plant Pat. No. 9,274 and issued on Sep. 5, 1995 are compared to 'POULscots' in Chart 1.

CHART 1

| | 'POULscots' | 'POULari' |
|---|---|---|
| Color of open flower, outer petals, middle zone. | Purple Group 76C | White Group 155D to 157D |
| Petalage | 25–30 | 55–75 |
| Upon opening, color basal petal spot, outer side | Yellow Group 4C | Greyed-Yellow Group 160D |

Parents:
*Seed parent.*—'POULari'.
*Pollen parent.*—'Mainzer fastnacht'.
Classification:
*Botanical.*—*Rosa hybrida.*
*Commercial.*—Hybrid tea.

FLOWER AND FLOWER BUD

Blooming habit: Recurrent.
Flower bud:
*Bud form.*—Pointed ovoid.
*Sepals.*—Appendages: Weak. Color: Upper surface is Yellow-Green Group 146A at margins and Yellow-Green Group 145A in interior. Lower surface is Yellow-Green Group 146A at margins and Yellow-Green Group 146C in interior. Size: 30 mm (l)×12 mm(w).
*Receptacle.*—Size: 12 mm (l)×10 mm(w). Color: Yellow-Green Group 144A. Shape: Funnel-shaped.
*Peduncle.*—Surface: Smooth. Very few hairs and prickles. Color: Yellow-Green Group 144A. Diameter: 5 mm. Length: 10 to 15 cm.
*Borne.*—Singularly. Few flowering shoots.
*Diameter.*—50 mm.
*Length.*—35 to 40 mm.
*Color.*—As sepals unfold, Purple Group 76D; at ¼ open, middle zone is Purple Group 76C and marginal zone is Purple Group 75B.
Flower bloom:
*Fragrance.*—Slightly spicy scent.
*Size.*—Large. Average flower diameter is 100–150 mm when open.
*Form.*—Shape of flower when viewed from the side: Upper part: Flat. Lower part: Flattened convex. Viewed from above: Irregularly rounded.
*Petalage.*—Double. Average range: 25–30 petals under normal conditions. Duration: On the plant, petals begin to fall after eight to ten days. On cut flowers, petals begin to fall at six to seven days.
Color:
*Petals.*—Inner Side: Middle zone: Purple Group 76C. Marginal zone: Purple Group 76C. Basal petal spot: Yellow Group 4C. Outer side: Middle zone: Purple Group 76C. Marginal zone: Purple Group 76C. Basal petal spot: Yellow Group 4C.
General tonality: On open flower Purple Group 76C. No change in general tonality of flower.
Petals:
*Petal reflex.*—Weak to medium.
*Undulation of margin.*—Medium.
*Size.*—30 to 35 mm (l)×30 mm (w).
*Quantity.*—25–30.
*Texture.*—Smooth.
*Shape.*—Deltoid. Apex is rounded, base is acute.

Reproductive organs:
*Pollen.*—None observed.
*Anthers.*—Size: 3 mm long. Color: Yellow-Orange Group 22A at margins; Yellow-Orange Group 20C in interior. Quantity: 55.
*Filaments.*—Color: Yellow-Green Group 150C. Length: 5 to 6 mm.
*Stigmas.*—Superior in location to anthers. Color: Green-Yellow Group 1C.
*Styles.*—Color: Red Group 54C. Length: 15 mm. Quantity: 85.
*Hip formation.*—Not observed.

PLANT

Plant growth: Upright, bushy, even growth; hardy and healthy. When grown as a budded field grown plant on *Rosa multiflora* understock, the average height of the plant is 60–80 cm and the average width is 40–50 cm.
Roots: Root initials are apparent 8 days after planting; roots begin to develop 10 to 14 days after planting.
Stems:
*Thorns.*—Incidence: 2 to 5 thorns per 10 cm of stem. Size: 5 to 8 mm. Shape: Deeply concave.
*Length.*—35 to 50 cm.
*Diameter.*—7 to 10 mm.
*Color.*—Young Wood: Yellow-Green Group 144B. Older Wood: Yellow-Green Group 143A.
Plant foliage:
*Typical leaf size.*—Medium. 150 mm (l)×130 mm.
*Quantity.*—Limited to average.
*Color.*—Mature Foliage: Upper Leaf Surface: Yellow-Green Group 147A. Lower Leaf Surface: Yellow-Green Group 148B. Juvenile foliage: Upper leaf surface: Yellow-Green Group 147A. Lower leaf surface: Yellow-Green Group 148B. Anthocyanin: Intonations of Greyed-Purple Group 187B and C on lower surface of both mature and juvenile foliage. Intonations also present on upper surface of juvenile foliage.
Plant leaves and leaflets:
*Stipules.*—Size: 15–17 mm (l)×5–7 mm (w). Color: Yellow-Green Group 144A and B. Stipitate glands: Located along margins. Anthocyanin: None.
*Petiole.*—Length: 12 to 16 mm. Color: Yellow-Green Group 146A. Underneath: Typically one small prickle and a limited number of stipitate glands. Margins: Stipitate glands present. Anthocyanin: Not present on juvenile foliage. Intonations along margins on mature foliage. Color: Greyed-Red Group 181A.
*Rachis.*—Color: Yellow-Green Group 146A. Underneath: Few prickles Margins: Stipitate glands present. Anthocyanin: On upper surface along margins of juvenile and mature foliage. Color: Greyed-Red Group 181A.
*Leaflet.*—Edge: Serrated. Shape: Ovate; apex is acute and base is rounded. Texture: Leathery. Venation: Reticulate. Size: 60 mm (l)×30 mm (w). Arrangement: Odd pinnate. Vein color: Yellow-Green Group 144A.

Disease resistance: Above average resistance to mildew, rust, black spot, and Botrytis under normal growing conditions in Fredensborg, Denmark and Hannover, Germany.

Cold hardiness: 'POULscots' has been found to be resistant to damage from cold, heat and drought damage in USDA Zone 7.

We claim:

1. A new and distinct variety of rose plant of the Hybrid Tea rose class, substantially as herein illustrated and described as a distinct and novel rose variety due to its abundant lavender flowers, disease resistance, and extended period of bloom.

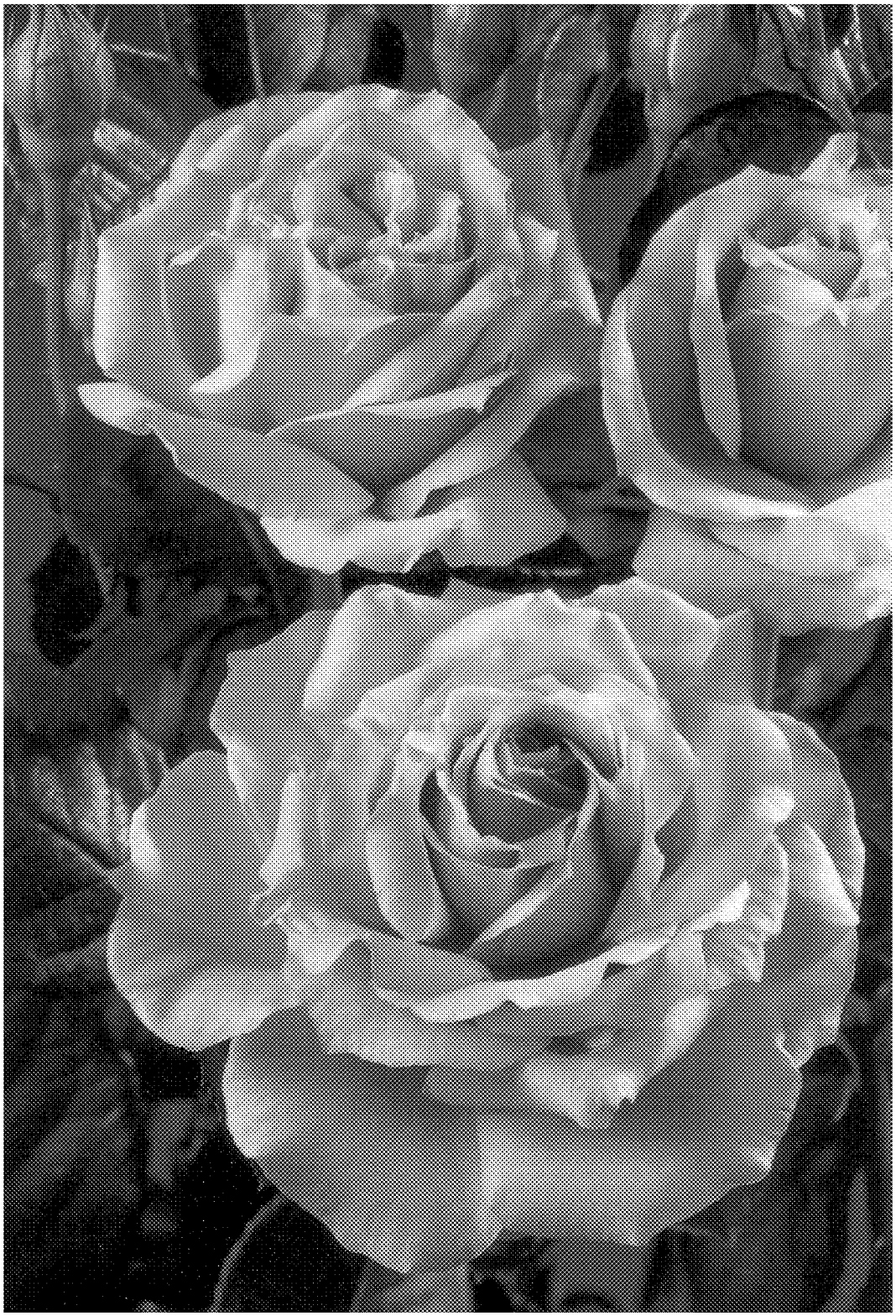

* * * * *